(12) United States Patent
Assadi-Porter et al.

(10) Patent No.: US 8,852,117 B2
(45) Date of Patent: Oct. 7, 2014

(54) IDENTIFICATION OF DISEASE CHARACTERISTICS USING ISOTOPE RATIOS IN BREATH

(71) Applicant: Wisconsin Alumni Research Foundation, Madison, WI (US)

(72) Inventors: Fariba M. Assadi-Porter, Fitchburg, WI (US); Mark E. Cook, Madison, WI (US); Warren P. Porter, Fitchburg, WI (US); Daniel E. Butz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 21 days.

(21) Appl. No.: 13/671,585

(22) Filed: Nov. 8, 2012

(65) Prior Publication Data

US 2013/0066224 A1 Mar. 14, 2013

Related U.S. Application Data

(62) Division of application No. 12/254,249, filed on Oct. 20, 2008, now Pat. No. 8,435,187, which is a division of application No. 11/290,024, filed on Nov. 30, 2005, now Pat. No. 7,465,276.

(51) Int. Cl.
*A61B 5/08* (2006.01)
*G01N 33/497* (2006.01)
*A61B 5/00* (2006.01)

(52) U.S. Cl.
CPC .............. *A61B 5/082* (2013.01); *G01N 33/497* (2013.01); *A61B 5/08* (2013.01); *A61B 5/411* (2013.01)
USPC ............................... 600/532; 73/23.3; 422/84

(58) Field of Classification Search
USPC ....................... 600/532, 529; 73/23.3; 422/84
See application file for complete search history.

(56) References Cited

U.S. PATENT DOCUMENTS

| | | |
|---|---|---|
| 4,298,347 A | 11/1981 | Walsh |
| 5,912,178 A | 6/1999 | Porter et al. |
| 5,944,670 A | 8/1999 | Katzman |
| 5,961,470 A | 10/1999 | Wagner et al. |
| 6,067,989 A | 5/2000 | Katzman |
| 6,110,122 A | 8/2000 | Wagner et al. |
| 6,186,958 B1 | 2/2001 | Katzman et al. |
| 6,248,078 B1 | 6/2001 | Risby et al. |

(Continued)

OTHER PUBLICATIONS

J. Jarvis, et al., The Effect of Food Matrix on Carbohydrate Utilization During Moderate Exercise, 24 Medicine and Science in Sports and Exercise 320-326 (1992).

(Continued)

*Primary Examiner* — Navin Natnithithadha
(74) *Attorney, Agent, or Firm* — Quarles & Brady LLP

(57) ABSTRACT

Methods are disclosed for distinguishing whether an animal is experiencing a bacterial infection or a viral infection. One monitors breath taken from the animal over time to measure the relative amount of a first breath stable isotope to a second breath stable isotope therein over time. A quick change in the isotope ratios within several hours from the likely infection is indicative of a bacterial infection. A delayed change in the isotope ratios, followed by periodic repeated alterations in the ratios, is indicative of viral infection. The methods are particularly efficient when using cavity ringdown spectroscopy for the monitoring. They may be used for monitoring a patient already admitted to a hospital, or for monitoring a patient initially complaining of adverse symptoms, or for triage, or for collectively monitoring a population of animals.

4 Claims, 3 Drawing Sheets

(56) References Cited

U.S. PATENT DOCUMENTS

| | | | |
|---|---|---|---|
| 6,491,643 B2 | 12/2002 | Katzman et al. | |
| 6,656,127 B1 * | 12/2003 | Ben-Oren et al. | 600/532 |
| 6,778,269 B2 | 8/2004 | Fink et al. | |
| RE38,728 E | 4/2005 | Katzman et al. | |
| 6,878,550 B2 | 4/2005 | Yatscoff et al. | |
| 6,890,305 B2 | 5/2005 | Irie et al. | |
| 7,014,612 B2 * | 3/2006 | Hubbard et al. | 600/532 |
| 7,255,677 B2 * | 8/2007 | Burch et al. | 600/300 |
| 7,338,444 B2 | 3/2008 | Ben-Oren et al. | |
| 7,465,276 B2 | 12/2008 | Assadi-Porter et al. | |
| 7,867,171 B2 | 1/2011 | Ben-Oren et al. | |
| 8,435,187 B2 * | 5/2013 | Assadi-Porter et al. | 600/532 |
| 2003/0171687 A1 * | 9/2003 | Irie et al. | 600/532 |
| 2005/0085740 A1 | 4/2005 | Davis et al. | |

OTHER PUBLICATIONS

M. Murphy, et al., Non-Invasive Assessment of Intraluminal Lipolysis Using a 13CO2 Breath Test, 65 Archives of Disease in Childhood 574-578 (1990).

E. Crosson, Stable Isotope Ratios Using Cavity Ring-Down Spectroscopy: Determination of 13C/12C for CO2 in Human Breath, 74 Anal. Chem. 2003-2007 (2002).

* cited by examiner

FIG. 3

VIRUS – CHICK – DELTA VALUE OVER TIME

*[Graph: DELTA VALUE (parts/mil) vs TIME (h), ranging from 45 to 185 hours on x-axis and 0 to -15 parts/mil on y-axis]*

IDENTIFICATION OF DISEASE CHARACTERISTICS USING ISOTOPE RATIOS IN BREATH

CROSS-REFERENCE TO RELATED APPLICATIONS

This application is a divisional of U.S. patent application Ser. No. 12/254,249 which was filed on Oct. 20, 2008 and is now U.S. Pat. No. 8,435,187, which in turn is a divisional of U.S. patent application Ser. No. 11/290,024 which was filed on Nov. 30, 2005 and is now U.S. Pat. No. 7,465,276.

STATEMENT REGARDING FEDERALLY SPONSORED RESEARCH/DEVELOPMENT

This invention was made with government support under AIO62327 awarded by the National Institutes of Health. The government has certain rights in the invention.

BACKGROUND OF THE INVENTION

The present invention relates to non-invasive methods for distinguishing bacterial infections from viral infections in humans and other animals by monitoring changes in isotopic ratios in breath.

Rapid determination of what type of infection is present in a patient complaining of symptoms associated with infection is very important in helping speed treatment, minimize the adverse effects of the infection, reduce the risk of spread of infection to others, and reducing the cost of ineffective treatment. Further, it helps avoid the risk of adverse side effects which may be inherent or associated with inappropriate treatments (e.g. if they are provided as a prophylactic measure or otherwise due to an inability to properly classify the nature of the infection at an early stage).

More recently there has been an increasing concern about the possibility of a biochemical attack by an agent that would not be known to medical personnel until several days after the attack. Where such an attack is suspected, it could well be desirable to screen a relatively large population of potential victims who may not have yet complained of symptoms, as a triage measure. In such a context it is particularly desirable to be able to spot exposure to an infectious agent very shortly after the exposure may have occurred.

There are currently a number of culturing and other techniques which are used to try to distinguish definitively between bacterial and viral infections. However, these can be time consuming, require the use of a sophisticated laboratory, be costly, and be otherwise disadvantageous. Hence, treating physicians will sometimes instead, or as an interim measure, prophylactically treat with drugs. For example, an antibiotic effective against a wide range of bacteria might be prophylactically prescribed for an infection even before it is clear that the infection is bacterial in nature.

Where the infection turns out to be viral instead, the cost of the drug will be unnecessarily incurred. Further, the patient will be exposed to the inherent side effect risks of an ineffective drug (e.g. some percentage of patients have severe allergic reactions to antibiotics).

Moreover, a decision to prophylactically treat with an unnecessary antibiotic can in some cases lead to the ineffectiveness of that antibiotic against certain future bacterial infections (a phenomenon known as antibiotic resistance development). This is particularly problematic for those bacterial infections where only a few antibiotics are known to be effective against the particular bacteria.

Researchers have previously studied the isotopic ratio of $^{13}C/^{12}C$ in human breath. In most of these experiments subjects were administered artificially labeled $^{13}C$ substrates before the study began. In one such experiment the researcher studied glucose metabolism during exercise as measured by $CO_2$ mass spectrometry after feeding $^{13}C$ labeled glucose to the subjects. Similarly, in U.S. Pat. No. 6,878,550 $^{13}C$-labeled $CO_2$ was monitored following ingestion of a $^{13}C$-enriched glucose source to study diabetic indications.

Researchers have also fed $^{13}C$-labeled urea to subjects in an attempt to detect bacteria which cause ulcers. Urease activity in ulcer bacteria converts urea to carbon dioxide and ammonia. Breath samples were collected from the test subjects and analyzed for the presence of labeled isotope in exhaled carbon dioxide.

Jarvis, et al., 24 Medicine and Science in Sports and Exercise 320-326 (1992) disclosed the effect of different food matrixes labeled with $^{13}C$ on breath $CO_2$ isotopic ratios during moderate exercise, and Murphy, et al., 65 Archives of Disease in Childhood 574-578 (1990) discloses the use of isotopic ratios in breath $CO_2$ to test for lipase activity in the human gut after feeding the subjects fat labeled with $^{13}C$. Of course, this research required the subject to be artificially dosed with an unusual isotope mix, and was not focused on testing the status of an isotopically unenriched population.

In U.S. Pat. No. 5,912,178 our laboratory reported that the catabolic state of animals (e.g. humans) consuming themselves is characteristic of the onset of infection (and certain other stresses). The disclosure of this patent, and of all other publications referred to herein, are incorporated by reference as if fully set forth herein.

In that patent our laboratory reported that even without isotope doping one could take samples from an animal of breath (and/or other specimens), evaluate certain isotope ratios (e.g. $^{13}C/^{12}C$ or $^{15}N/^{14}N$) in those specimens, and then use information derived therefrom to determine if the animal was undergoing a catabolic state. For example, that patent describes the measurement of changes in the $^{13}C/^{12}C$ isotopic ratio of exhaled carbon dioxide using mass spectrometry.

That patent also described applications in connection with veterinary monitoring. Hence, such technology has applicability to animal agriculture as well.

U.S. Pat. No. 4,298,347 discussed a method for analyzing isotopic ratios in exhaled carbon dioxide, and that was useful in connection with our laboratory's mass spectrometry work. The method involved a solvent and an organometallic compound that reacted with gaseous carbon dioxide and formed a soluble carbonyl compound which has a unique and well separated infrared spectral peaks.

Of course, mass spectrometry equipment is relatively expensive, can require considerable training, and is often unsuitable for installation and use in small offices or in portable medical facilities (e.g. an emergency vehicle). Thus, in E. Crosson, Stable Isotope Ratios Using Cavity Ring-Down Spectroscopy: Determination of $^{13}C/^{12}C$ for Carbon Dioxide in Human Breath, 74 Anal. Chem. 2003-2007 (2002) there was a discussion of the desirability of using cavity ring-down spectrometers employing a near-IR external cavity diode laser to measure such $^{13}C/^{12}C$ ratios in human breath. It was noted that this type of equipment is more compact, less expensive, and more portable than conventional mass spectrometry equipment, and thus the use of this type of equipment could render more practical such measurements for medical diagnostic purposes. The article also noted that it was possible that such equipment could create a breath test for the presence of a particular bacteria associated with stomach ulcers if the patient ingested $^{13}C$ labeled urea (a doping environment).

For further discussion of use of cavity ring-down spectroscopy to analyze stable isotope ratios in carbon dioxide see generally T. Spence et al., A Laser Locked Cavity Ringdown Spectrometer Employing An Analog Detection Scheme, 71 Review of Scientific Instruments 347-353 (2000).

While the art had previously taught that stable isotope ratios would change in the presence of stressing of the animal (such as by catabolism caused by infection), the art had not previously taught a way to distinguish bacterial from viral infection based on monitoring such ratios, much less in the context where the patient was isotopically unenriched (particularly doped with isotopes for the purpose of the experiment).

Hence, improved methods are desired for distinguishing bacterial from viral infection.

SUMMARY OF THE INVENTION

Our work provides human health care professionals and veterinarians with early and effective indicators of bacterial and viral infection, preferably using a highly accurate, fast, relatively inexpensive, and easy to use isotopic breath analyzer.

In one aspect the invention provides methods of distinguishing whether an animal is experiencing a bacterial infection. One monitors breath taken from the animal over time to measure the relative amount of a first isotope to a second isotope therein over time. The first and second isotopes are preferably the pair of $^{13}C$ and $^{12}C$, but might also be alternatively the pair of $^{15}N$ and $^{14}N$, or the pair of $^{17}O$ and $^{16}O$, or a pair of sulphur isotopes (e.g. $^{32}S$ and $^{34}S$; $^{33}S$ and $^{36}S$).

Based on a comparison of (i) changes to the relative amount of the first isotope to the second isotope over time, with (ii) a known pattern of changes of the relative amount of the first isotope to the second isotope in the presence of bacterial infection one determines whether bacterial infection is present. In this regard, we have discovered that bacterial infections will change the ratios very quickly after exposure (e.g. preferably less than 12 hours after exposure, even more preferably less than 4 hours after exposure, most preferably within 1 or 3 hours after exposure).

The monitoring could begin at an annual physical (when no infection symptoms are noticed by the patient or the doctor to obtain a baseline reading for the patient). For example, this could be when the patient is not running an elevated temperature. Alternatively, it could begin when a patient having an elevated temperature first meets with a physician.

While the above methods could be conducted by comparing just two breath specimens if appropriately timed (e.g. the first at the time of infection and the second about two hours later), it is preferred that more specimens be monitored over time to confirm the pattern. In this regard, monitoring for four days when a patient is hospitalized for that period will be able to confirm the diagnosis.

This type of monitoring could become quite routine in an ICU environment where the patient is otherwise being continuously monitored. In other cases, multiple visits to the medical facility (e.g. a follow-up visit) would provide the opportunity for the monitoring.

In preferred forms, the monitoring extends over a long enough period (e.g. 3-7 days) to permit one to conduct a comparison of (i) changes to the relative amount of the first isotope to the second isotope over time, with (ii) a known pattern of changes of the relative amount of the first isotope to the second isotope in the presence of viral infection determining whether viral infection is present.

While these methods could be performed using mass spectroscopy or other equipment, it is highly preferred when carbon isotope ratios are involved to use cavity ringdown spectroscopy to determine the changes in the relative amounts. This is because this equipment is relatively inexpensive, has few training requirements, and typically is quite compact.

While human diagnostic applications are a primary utility of the present invention, it is also intended to use the present invention to monitor the cause of infection of a population of agricultural animals (e.g. chickens in a chicken coop; young cows or other non-human mammals in an enclosed environment). A baseline reading could establish the base ratio for the population, and the change in that ratio over time would be indicative of the cause of the disease.

In another aspect the invention provides methods of distinguishing whether an animal is experiencing a viral infection. As above, breath taken from the animal over time is used to measure the relative amount of a first isotope to a second isotope therein over time, wherein the first and second isotopes are preferably the pair of $^{13}C$ and $^{12}C$, but might also be alternatively the pair of $^{15}N$ and $^{14}N$, or the pair of $^{17}O$ and $^{16}O$ or a pair of sulphur isotopes (e.g. $^{32}S$ and $^{34}S$; and $^{36}S$).

Based on a comparison of (i) changes to the relative amount of the first isotope to the second isotope over time, with (ii) a known pattern of changes of the relative amount of the first isotope to the second isotope in the presence of viral infection one can determine whether viral infection is present.

In yet another aspect the invention provides methods for triaging a selected population of patients who are suspected of having been exposed to an infectious biological agent. One monitors with cavity ringdown spectroscopy breath taken from each patient in that selected population over time to measure the relative amount of a first isotope to a second isotope therein over time, wherein the first and second isotopes are the pair of $^{13}C$ and $^{12}C$. For each such patient, based on comparisons of (i) changes to the relative amount for them of the first isotope to the second isotope over time, with (ii) a known pattern or patterns of changes of the relative amount of the first isotope to the second isotope in the presence of bacterial infection one can determine whether that patient has a bacterial infection. Based thereon one prioritizes (triages) treatment of said population of patients.

In yet other forms, the method involves monitoring an overall population simultaneously, or monitoring the rate of change of such isotope ratios in addition to the direction and pattern of change.

It should be appreciated that the present invention permits one to distinguish bacterial from viral infections, and in the case of bacterial infections to make that diagnosis in some cases even before the patient has developed signs of infection that are readily detectable by the patient. This can be achieved quickly at relatively low cost (e.g. without a complex laboratory having to grow up a culture). The equipment to achieve this is in fact so compact that it might be used on certain emergency vehicles designed for first response to suspected bio-terror attacks.

As the diagnosis of the presence or absence of a bacterial infection occurs quickly, the need for prophylactically treating with an antibiotic pending confirmation of the nature of the infection is greatly reduced. Hence, the incidence of antibiotic resistance development should be reduced as the practice of the present invention becomes more widespread.

While we have tested certain infectious agents (e.g. as described in the experiments below), it is expected that the methods of the present invention will be broadly useful in distinguishing bacterial from viral infection. In this regard, as discussed below, the theoretical basis for the results we are seeing are believed common to bacteria and viruses as groups of infectious agents.

We propose using the present invention to monitor for the presence of a wide variety of bacteria that commonly cause infection, such as gram positive and gram negative bacteria that commonly cause infection. By way of example, and not limitation, this could include bacteria such as *Listeria* sp., *Salmonella* sp., *Pneumococcus* sp., *Staphylococcus* sp, *Clostridium* sp., *Escherichia* sp., *Pseudomonas* sp., bacterial meningitis, and *Streptococcus* sp. Protozoan and fungal infections that have systemic effects are also intended to be monitored in similar fashion.

Similarly, we propose using the present invention to monitor for the presence of a wide variety of viruses that commonly cause infection, such as a wide variety of DNA and RNA viruses. By way of example, and not limitation, this could include hepatitis C, influenza, rhinovirus, measles, Epstein-Barr, pox, and viral meningitis.

These and still other advantages of the present invention will be apparent from the description that follows. The following description is merely of the preferred embodiments. Thus, the claims should be looked to in order to understand the full scope of the invention.

DESCRIPTION OF THE DRAWINGS

FIG. 3 illustrates the time course for isotope ratios, presented as delta values, for healthy chickens that were given viral vaccine as a viral challenge.

DESCRIPTION OF THE PREFERRED EMBODIMENTS

Theoretical Overview

Figure 1:
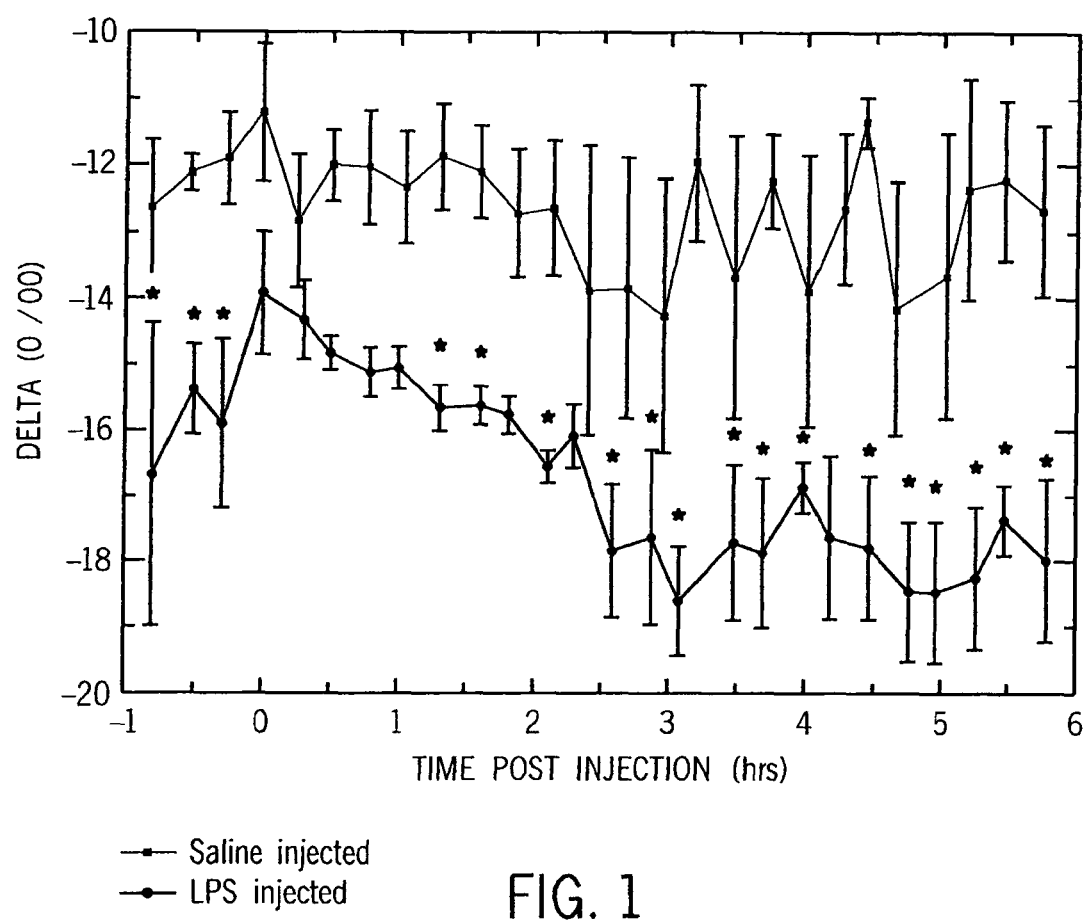
FIG. 1 illustrates the time course for isotope ratios, presented as delta values, for a healthy control mammal, as compared to the mammal given bacterial lipopolysacchride (LPS) as a bacterial challenge.

Fighting infections (particularly those that are bacterial in origin) requires rapid protein breakdown to supply the high energy and raw material requirements (e.g. amino acids) for antibody production and other anti-infection response. Certain isotopic ratios of proteins, fats, and carbohydrates stored in body tissues differ from the isotopic ratio of metabolized food, and when a catabolic state is induced by infection the body begins to consume stored tissue, which (due to the different ratios in the stored tissue) results in a change in the ratios in breath (e.g. exhaled $^{13}CO_2$ content).

In particular the heavy isotope to light isotope ratios become more positive in the presence of infection, such that the "delta" representation thereof (as defined below) becomes more negative in response to infection. The change is believed to be a direct reflection of the increasing use of body tissue for "fuel". Absent extreme stress such as an infection, the lighter isotopes are normally preferentially oxidized for energy and appear in breath. The heavier isotopes then are left behind and stored in body tissues. We refer to this phenomenon more broadly as atom fractionation.

During bacterial infection immune responses (acute and involving the innate immune system) to the invasion are marked by a sudden release of catabolic cytokines within the first hour of infection. These cytokines consist of tumor necrosis factor (TNF), and interleukins (IL) 1 and 6. These three cytokines result in the rapid redistribution of body nutrients, such as amino acids.

For example, TNF and IL-1 will induce the degradation of skeletal muscle resulting in a release of amino acids that can be used to make immune and inflammatory acute phase protein or use as fuel. The step of fractionation of the carbon flow of molecules occurs as amino acids flow toward new proteins, they are burned instead as fuel.

In contrast, the cytokines associated with early stages of viral infections cause the release of different cytokines, namely the interferons, which fail to elicit an acute phase response. Hence carbon fractionation yields yet a different pattern, a pattern typically more linked to the reproductive stage of the virus.

We have learned that there is a distinct change in isotope ratio amounts within about 2 hours after bacterial challenge begins, followed by relatively stable, albeit changed from the unchallenged animals, ratios for a prolonged period. In contrast, a virally challenged host exhibits a series of periodic modifications, beginning significantly later (e.g. 2-3 days). We expect a similar pattern for isotope ratios with respect to other atom pairs present in breath.

Importantly, we have also learned that in the case of bacterial infection, the breath becomes "lighter" at a greater rate of speed than during a viral infection. Hence, the speed of change, as well as the presence or absence of the repeated spikes in the ratio pattern indicative of a viral life cycle, are indications of the type of infecting agent.

In sum, bacterial immune stimuli create a very rapid and strong response by the immune system that involves a rapid protein (typically muscle) breakdown. In contrast, viral infections involve an invasion of the cells in the body by the viruses, a takeover of the cellular machinery to make new viral particles (which can take considerable time), and then ultimately a rupture of the infected cells to release replicated viruses for another invasion process. This cycle is repeated periodically, at generally regular intervals. For many viruses the cycle is about a 24-hour interval after each rupture.

For humans, we propose in a preferred case to obtain a base line reading for a patient at an annual physical or at another opportunity when the patient is otherwise at a medical facility and not complaining of symptoms of illness. Alternatively, the first reading could be when a patient first complains of infection type symptoms (e.g. particularly elevated temperature). Then repetitive readings can be taken, preferably over a several day period.

With respect to a hospitalized patient, this might be done every hour for the first day, followed by twice a day thereafter. However, the frequency of monitoring will change depending on patient condition and early results.

For confined non-human animals, or populations of such animals, regular hourly monitoring could be conducted on a continuous basis. Alternatively, similar principles could be applied with respect to monitoring the health of humans in an apartment building on an overall basis.

EXPERIMENTAL

We have infected diverse types of animals with bacterial (endotoxin) and viral (attenuated virus) challenges, and monitored via cavity ringdown spectroscopy the changes in stable isotope ratios in their breath. The endotoxin is a glycolipid component of the cell wall from gram-negative bacteria, which induces a strong immune response. The virus was in the form of an attenuated viral vaccine.

We expect a similar host response process for live whole bacteria and virus. For example, we have showed in our laboratory's earlier experiments (using mass spectrometer measurements) that live bacteria and isolated bacterial cell walls (LPS) each generate indistinguishably similar responses in mice with respect to isotope ratios.

This isotope ratio is being reported herein as a "delta" value which is expressed in parts per mil (parts per thousand) in accordance with the following equation:

$$\delta(^{13}C/^{12}C) = \frac{(^{13}C/^{12}C)_{measured} - (^{13}C/^{12}C)_{PDB}}{(^{13}C/^{12}C)_{PDB}}$$

Measurements of isotopic ratios at concentrations ranging from 0.5% to 3% are typical in breath.

Example 1

FIG. 1 illustrates the time course for delta values for a healthy mammal versus one that was given a bacterial cell wall component (LPS) as an immune stimulus. The data illustrates that the carbon isotope ratios presented as delta values becomes more negative significantly below controls within about two hours of the time the LPS immune stimulus entered the organism. We would expect similar results for other isotope pairs.

At time zero mice (n=5 per group) were injected i.p. with either bacterial cell walls (LPS at 1 mg/kg body weight) or sterile saline (vehicle), and placed in a metabolic chamber. Continuous airflow through the chamber was sampled approximately every 15 minutes by a cavity ring-down spectrometer (CRDS) and the isotopic ratio of $^{13}C/^{12}C$ (delta) was measured. Results were analyzed using SAS proc mixed accounting for autocorrelation of repeated measures. Stars represent statistically significant differences between treatments at a given time-point with $p<0.05$.

Example 2

Figure 2:
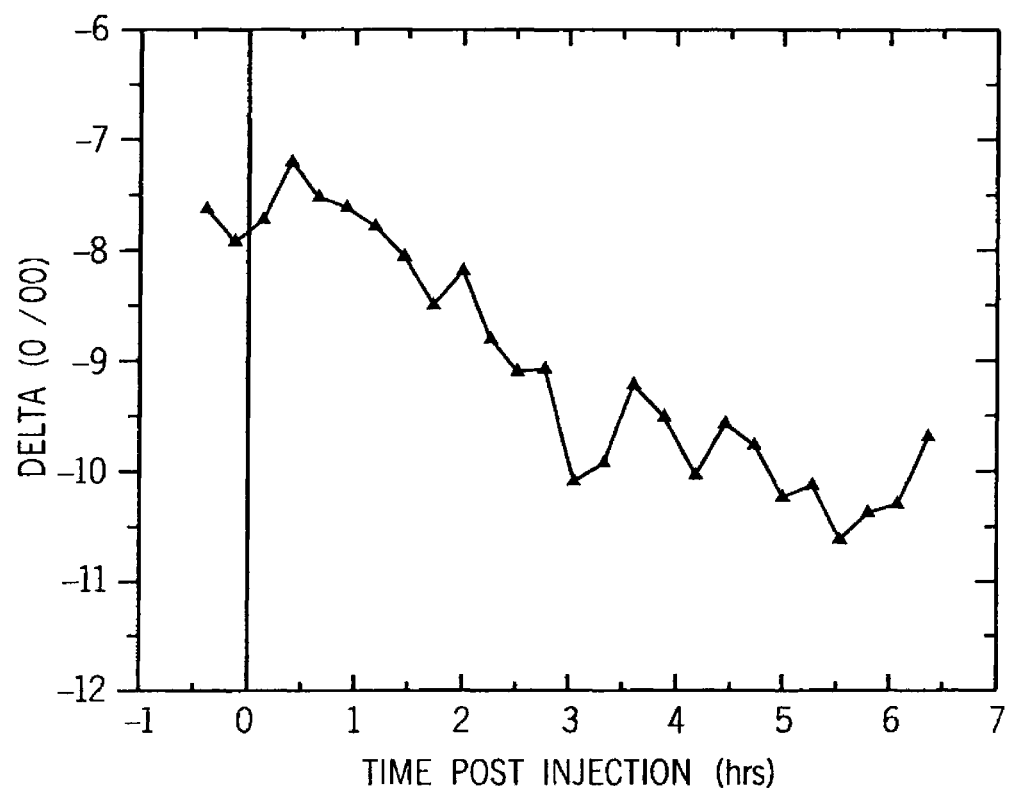
FIG. 2 illustrates the time course for isotope ratios, presented as delta values, for chickens that were given bacterial lipopolysacchride (LPS) as a bacterial challenge.

FIG. 2 shows that the bacterial cell wall immune stimulus response is similar between the Example 1 mice experiments and the Example 2 chickens. It confirms that a chicken given the same kind of bacterial cell wall injection also has a significant negative change in breath stable isotope delta values within two hours of the administration of the bacterial cell wall immune stimulus. The chickens serve as their own control with the normal pre-injection stable isotope breath variation between approximately −7 and −9 delta.

Example 3

FIG. 3 shows that the isotope ratio response to a viral infection is much slower than to a bacterial infection, and it has different, and distinguishing, characteristics. It takes well over a day (e.g. often about 80 hours) for the first appreciable viral response in the isotope ratio to occur. This is contrasted with the much quicker isotope ratio response (e.g. about 2 hours) for bacteria.

In this experiment food was initially withheld to make the chick hungry and thirsty. A viral agent was administered in drinking water. After the chick had consumed the water with the viral agent, food was restored and the experiment continued. Approximately 80 hours into the experiment the first significant decline in delta values occurred. A partial recovery period then ensued. A sudden more negative result and recovery pattern was then periodically repeated.

Example 4

For human clinical use we would propose that a small cavity ringdown spectroscopy machine (e.g. available from Picarro or Tiger Optics) provide measurements of a patient's breath initially every 15 minutes or less after monitoring begins by sampling from a flow-through mask. Where a baseline value is available from the patient's records, the readings could be compared to that. If not, the pattern of the readings could be evaluated to look for a reduced level from average levels in the population, and/or the characteristics of a viral infection pattern developing over a several day period.

The normal variation of breath delta values of carbon stable isotopes in carbon dioxide is approximately plus or minus one delta value for healthy mammals. The onset of bacterial infection, i.e. catabolic state, results in breath carbon isotope delta values quickly dropping beneath the normal range by up to three delta. This is a significant decline below the normal range of variation, and thus could help identify a bacterial infection even when the source of infection occurred a day or two before monitoring begins. For other isotope pairs a similar differential in delta values is expected.

Example 5

As an additional example we propose to establish an enclosed chicken coop with a confined population of growing chickens. The air inside the coop could be refreshed at a constant rate and periodically sampled from a consistent location, with changes in isotope ratios being monitored. Again, one would look for the characteristic bacterial or viral indicia in the pattern of the ratios to distinguish bacterial from viral infection. However, here the population as a whole is monitored.

Example 6

As an additional example we propose to monitor the nitrogen ratios in human breath.

Other

As data is collected for various specific types of viral infections or bacterial infections, we expect to be able to tell from that data more information characteristic of specific viruses or bacteria. For example, some specific types of viral infections are expected to have particular characteristic amplitudes for the periodic pattern. Moreover, the combination of the ratio information, with other marker or other information which becomes available to the medical practitioner will help further characterize the nature of the infection.

Further, the present invention should allow a practitioner to watch the progress of an infection as dynamic changes occur during the infectious response. This may include monitoring the effectiveness of drugs or other therapies. For example, as the body recovers from an infection it is expected that the ratios would return to normal levels.

Hence, the invention is not to be limited by the specific embodiments described herein. Thus, the claims should be looked to in order to judge the full scope of the invention.

INDUSTRIAL APPLICABILITY

The invention provides methods of monitoring animal health, with particular capability for non-invasively testing to distinguish bacterial from viral infections.

We claim:

1. A method of triaging a population of patients suspected of having been exposed to an infectious material, comprising:

monitoring, with a cavity ring-down spectrometer, breath taken from each patient in the population over time to measure a relative amount of a first isotope to a second isotope therein over time, wherein the first and second isotopes are a pair of $^{13}C$ and $^{12}C$;

for each patient, based on comparisons of (i) changes to the relative amount for them of the first isotope to the second isotope over time, with (ii) a known pattern or patterns of changes of the relative amount of the first isotope to the second isotope when there is bacterial infection, determining, with a computer, whether the patient has a bacterial infection; and based on said determining, triaging medical treatment of said population of patients.

2. The method of claim 1, wherein the patients are mammals.

3. The method of claim 2, wherein the patients are humans.

4. The method of claim 1, wherein the spectrometer is capable of measuring the relative amount of the first isotope to the second isotope in a patient's breath at fifteen minute intervals or less.

\* \* \* \* \*